United States Patent
Jones et al.

(10) Patent No.: US 9,204,897 B2
(45) Date of Patent: Dec. 8, 2015

(54) SURGICAL CUTTING GUIDE

(71) Applicant: Zimmer, Inc., Warsaw, IN (US)

(72) Inventors: Nolan C. Jones, Warsaw, IN (US); Jeffery A. VanDiepenbos, Syracuse, IN (US)

(73) Assignee: Zimmer, Inc., Warsaw, IN (US)

( * ) Notice: Subject to any disclaimer, the term of this patent is extended or adjusted under 35 U.S.C. 154(b) by 530 days.

(21) Appl. No.: 13/720,251

(22) Filed: Dec. 19, 2012

(65) Prior Publication Data
US 2013/0158556 A1 Jun. 20, 2013

Related U.S. Application Data

(60) Provisional application No. 61/577,466, filed on Dec. 19, 2011.

(51) Int. Cl.
| | | |
|---|---|---|
| A61B 17/56 | (2006.01) | |
| A61B 17/15 | (2006.01) | |
| A61B 17/17 | (2006.01) | |

(52) U.S. Cl.
CPC ............ *A61B 17/56* (2013.01); *A61B 17/15* (2013.01); *A61B 17/154* (2013.01); *A61B 17/155* (2013.01); *A61B 17/157* (2013.01); *A61B 17/17* (2013.01); *A61B 2017/564* (2013.01); *A61B 2017/565* (2013.01)

(58) Field of Classification Search
CPC .... A61B 17/15; A61B 17/154; A61B 17/155; A61B 17/157; A61B 17/56; A61B 2017/564; A61B 2017/565
See application file for complete search history.

(56) References Cited

U.S. PATENT DOCUMENTS

| | | | | |
|---|---|---|---|---|
| 5,484,446 | A | * | 1/1996 | Burke et al. .................. 606/87 |
| 5,486,178 | A | | 1/1996 | Hodge |
| 5,562,674 | A | * | 10/1996 | Stalcup et al. ................ 606/88 |
| 5,830,216 | A | * | 11/1998 | Insall et al. .................... 606/88 |
| 7,794,467 | B2 | | 9/2010 | McGinley et al. |
| 7,959,637 | B2 | | 6/2011 | Fox et al. |
| 8,277,450 | B2 | | 10/2012 | Dees, Jr. et al. |
| 8,333,772 | B2 | | 12/2012 | Fox |
| 2006/0241634 | A1 | | 10/2006 | Tuttle et al. |
| 2007/0213738 | A1 | | 9/2007 | Martin et al. |
| 2009/0204115 | A1 | | 8/2009 | Dees, Jr. et al. |
| 2010/0094301 | A1 | | 4/2010 | Dees, Jr. et al. |
| 2010/0121334 | A1 | * | 5/2010 | Couture et al. ............... 606/87 |
| 2010/0241126 | A1 | | 9/2010 | Ghijselings |
| 2011/0251618 | A1 | | 10/2011 | Mcallister et al. |
| 2013/0012941 | A1 | | 1/2013 | Dees, Jr. et al. |

* cited by examiner

*Primary Examiner* — Larry E Waggle, Jr.
(74) *Attorney, Agent, or Firm* — Schwegman Lundberg & Woessner, P.A.

(57) ABSTRACT

Tools or other instruments can be used by a surgeon to complete an orthopedic procedure. One tool can include a resection tower and a valgus guide. The resection tower can include a cutting block and a dial coupled with the cutting block. The resection tower can be configured such that rotational movement of the dial, about an axis, effectuates movement of the cutting block along a plane substantially parallel with the axis. The dial, when rotated in a first direction, can move between a first position, which corresponds to a minimum cutting depth of the cutting block, and a second position, which corresponds to a maximum cutting depth of the cutting block. The valgus guide can be coupled with the resection tower and includes a rotatable member. The rotatable member can include an angular surface with one or more variable depth splines providing varus/valgus angle adjustment of the cutting block.

19 Claims, 14 Drawing Sheets

SURGICAL CUTTING GUIDE

CLAIM OF PRIORITY

This non-provisional patent application claims the benefit of priority under 35 U.S.C. §119(e) to U.S. Provisional Pat. application Ser. No. 61/577,466, entitled "RESECTION TOWER AND VALGUS ALIGNMENT GUIDE," filed on Dec. 19, 2011, which is hereby incorporated by reference in its entirety.

BACKGROUND

Tools or other instruments can be used by a surgeon to complete an orthopedic procedure. For example, a surgical cutting guide can be used during an orthopedic procedure to prepare a bone for a prosthetic implant.

SUMMARY

The present disclosure is directed to surgical cutting guide systems and methods for the placement of a cutting block on a bone during an orthopedic procedure. Using the surgical cutting guide systems and methods, a surgeon can quickly and easily position the cutting block at a particular depth and at a particular varus/valgus angle during the orthopedic procedure.

The present inventors have recognized, among other things, that existing systems and methods for adjusting a depth or a varus/valgus angle of a cutting block fail to provide a surgeon with certain speed and ease of use features, such as fast return depth adjustment and minimal rotation to reach maximum varus/valgus angles. The present inventors have further recognized that cutting block adjustment systems and methods can be made more efficient by leveraging a previously positioned intramedullary rod or nail for placement purposes.

The present systems and methods provide or use a resection tower and a valgus guide. The resection tower can include a cutting block and a dial coupled with the cutting block. The resection tower can be configured such that rotational movement of the dial about an axis, effectuates movement of the cutting block along a plane substantially parallel with the axis. The dial, when rotated in a first direction, can move between a first position, which corresponds to a minimum cutting depth of the cutting block, and a second position, which corresponds to a maximum cutting depth of the cutting block. The dial, when rotated in the first direction past the second position, causes the cutting block to return directly to the minimum cutting depth.

The valgus guide can be coupled with the resection tower and includes a rotatable member and a collet lock. The rotatable member can include an angular surface with one or more variable depth splines providing varus/valgus angle adjustment of the cutting block. The variable depth splines are configured such that rotation of the rotatable member less than 90 degrees can effectuate adjustment of the cutting block to a maximum varus/valgus angle. The collet lock is configured to couple the valgus guide to an intramedullary rod or nail and thereby, advantageously provides a surgeon with an intramedullary securement means, instead of pinning, for accurate placement of the cutting block. An amount of time to secure the valgus guide to the intramedullary rod or nail via the collet lock can be less than an amount of time to pin the valgus guide to a bone.

To better illustrate the surgical cutting guide systems and methods disclosed herein, a non-limiting list of examples is provided here:

In Example 1, a system comprises a resection tower including a cutting block, having a slot for guiding a cutting tool, and a dial, coupled with the cutting block such that rotational movement of the dial about an axis effectuates movement of the cutting block along a plane substantially parallel with the axis. The dial, when rotated in a first direction, is configured to move between a first position, corresponding to a minimum cutting depth of the slot, and a second position, corresponding to a maximum cutting depth of the slot. The dial, when rotated in the first direction past the second position, is configured to cause the slot to return directly to the minimum cutting depth.

In Example 2, the system of Example 1 is optionally configured such that the dial includes a first side, a second side, and an internal surface defining a bore extending about the axis between the first and second sides. The internal surface includes a helical groove extending from a first point, adjacent to the first side, to a second point, adjacent to the second side.

In Example 3, the system of Example 2 is optionally configured such that an axial distance between the first point and the second point along the internal surface substantially corresponds to a distance between the minimum cutting depth of the slot and the maximum cutting depth of the slot.

In Example 4, the system of any one or any combination of Examples 2 or 3 is optionally configured such that the helical groove extends less than 360 degrees around the internal surface.

In Example 5, the system of any one or any combination of Examples 2-4 is optionally configured such that the internal surface includes a substantially straight groove extending from the first point to the second point.

In Example 6, the system of any one or any combination of Examples 2-5 is optionally configured such that the resection tower further includes a pin longitudinally disposed in a direction substantially parallel to the axis. The pin includes a first end portion extending through the bore and a second end portion releasably coupled with the cutting block.

In Example 7, the system of Example 6 is optionally configured such that the pin includes a projection extending from the first end portion at an angle relative to the longitudinal disposition of the pin. The projection is configured to move along the helical groove from the first point to the second point as the dial is rotated in the first direction from the first position to the second position, respectively.

In Example 8, the system of Example 7 is optionally configured such that the projection is configured to move along a substantially straight groove extending from the first point to the second point as the dial is rotated in the first direction from the second position, respectively.

In Example 9, the system of any one or any combination of Examples 6-8 is optionally configured such that the resection tower further includes a base, to which the dial and the pin are coupled, and a locking mechanism configured to releasable couple the second end portion of the pin to the cutting block. The locking mechanism includes a locking lever, a plunger, and a locking ball. The locking lever is movable between a locked position and an unlocked position and is coupled with the first end portion of the pin. The plunger extends within the pin and includes a locking ramped surface located near the second end portion of the pin. The locking ball is configured to be engageable with the locking ramped surface and secures engagement between the pin and the cutting block when the locking lever is in the locked position.

In Example 10, the system of Example 9 optionally further includes a resilient member extending around the plunger from a first end to a second end. The resilient member is configured to transition from a compressed state to an uncompressed state as the dial is rotated from the second position to the first position.

In Example 11, the system of any one or any combination of Examples 1-10 optionally further includes a valgus guide, coupled with the resection tower, including a rotatable member having an angular surface with one or more variable depth splines.

In Example 12, the system of Example 11 is optionally configured such that the valgus guide further includes a valgus alignment guide and one or more spherical contacts. The valgus alignment guide couples the valgus guide with the resection tower and includes one or more depressions. The one or more spherical contacts are positioned partially within the one or more depressions and configured to engage with the one or more variable depth splines.

In Example 13, the system of any one or any combination of Examples 11 or 12 is optionally configured such that the rotatable member, when rotated, effectuates adjustment of a varus/valgus angle of the cutting block. The valgus guide is configured such that a maximum varus/valgus angle is reached when the rotatable member is rotated less than 90 degrees.

In Example 14, the system of Example 13 is optionally configured such that the rotatable member includes a plurality of angle reference marks corresponding to a plurality of varus/valgus angles. The plurality of angle reference marks include at least a center reference mark, corresponding to a minimum varus/valgus angle, a right maximum reference mark, corresponding to a maximum right varus/valgus angle, and a left maximum reference mark, corresponding to a maximum left varus/valgus angle.

In Example 15, the system of Example 14 is optionally configured such that a space between each of the plurality of angle reference marks is identical.

In Example 16, the system of any one or any combination of Examples 11-15 is optionally configured such that a thickness of the rotatable member is greatest at a first point on the circumference of the angular surface and is smallest at a second point, diametrically opposite the first point, on the circumference of the angular surface.

In Example 17, the system of Example 16 is optionally configured such that the angular surface comprises a first variable depth spline and a second variable depth spline. The first and second variable depth splines are positioned equidistant from a center line connecting the first and second points on the circumference of the angular surface.

In Example 18, the system of any one or any combination of Examples 16 or 17 is optionally configured such that the one or more variable depth splines taper in width from a first end, near the first point on the circumference, to a second end, near the second point on the circumference. The one or more variable depth splines can form an arc between the first and second ends.

In Example 19, the system of Example 18 is optionally configured such that the one or more variable depth splines have a first depth at the first end and have a second depth at the second end. The first depth is greater than the second depth.

In Example 20, the system of any one or any combination of Examples 11-19 is optionally configured such that the angular surface forms an angle relative to a plane perpendicular to an axis of the rotatable member. The angle can correspond to a maximum right varus/valgus angle of the cutting block and to a maximum left varus/valgus angle of the cutting block.

In Example 21, the system of any one or any combination of Examples 11-20 is optionally configured such that the valgus guide includes a collet lock configured to couple to an intramedullary rod or nail.

In Example 22, a method comprises sliding a system including a resection tower, having a cutting block and a dial, and a valgus guide, having a rotatable member, over an intramedullary rod or nail; turning the rotatable member to adjust a varus/valgus angle of the cutting block, including engaging one or more spherical contacts with one or more variable depth splines on an angular surface of the rotatable member; and turning the dial to adjust a cutting depth of the cutting block.

In Example 23, the method of Example 22 is optionally configured such that turning the dial includes turning the dial in a first direction from a first position, corresponding to a minimum cutting depth of the cutting block, to a second position, corresponding to a maximum cutting depth of the cutting block.

In Example 24, the method of any one or any combination of Examples 22 or 23 is optionally configured such that turning the dial in the first direction further includes turning the dial past the second position, thereby directly returning the cutting block to the minimum cutting depth of the cutting block.

In Example 25, the method of any one or any combination of Examples 22-24 is optionally configured such that turning the rotatable member includes turning the rotatable member less than 90 degrees and positioning the cutting block at a maximum varus/valgus angle.

In Example 26, the surgical cutting guide system or method of any one or any combination of Examples 1-25 is optionally configured such that all elements or options recited are available to use or select from.

These and other examples and features of the present surgical cutting guide systems and methods will be set forth in part in the following Detail Description. This Summary is intended to provide an overview of the present subject matter—it is not intended to provide an exclusive or exhaustive explanation. The Detailed Description is included to provide further information about the present surgical cutting guide systems and methods.

BRIEF DESCRIPTION OF THE DRAWINGS

In the drawings, which are not necessarily drawn to scale, like numerals can be used to describe similar components in different views. The drawings illustrate generally, by way of example, but not by way of limitation, various embodiments discussed in the present patent document.

DETAILED DESCRIPTION

Figure 1:
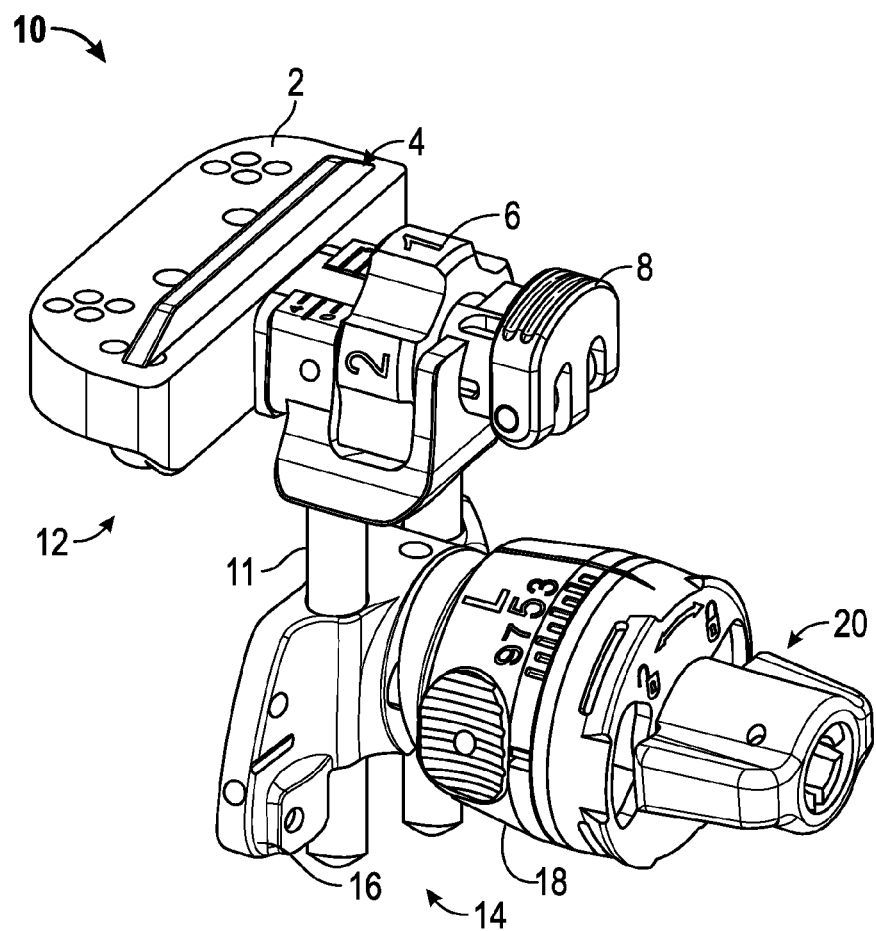
FIG. 1 illustrates a perspective view of a system including a resection tower and a valgus guide, in accordance with at least one example of the present disclosure.

FIG. 1 illustrates a perspective view of a system 10 including a resection tower 12 and a valgus guide 14, in accordance with at least one example of the present disclosure. The system 10, according to the present disclosure, can be used to position a cutting block 2 at a particular depth and at a particular varus/valgus angle on a bone during an orthopedic procedure. For example, the system 10 can be used to prepare a distal end of a femur or a proximal end of a tibia for a knee arthroplasty procedure, a proximal end of a femur for a hip arthroplasty procedure, or a proximal end of a humerus for a shoulder arthroplasty procedure.

The resection tower 12 can include a cutting block 2 having a slot 4 to guide one or more cuts to be made by a cutting instrument, such as a saw, to remove a portion of a bone. The resection tower 12 can include a dial 6 operatively coupled with the cutting block 2. Rotational movement of the dial 6, in a first direction, can effectuate movement of the cutting block 2 and adjust a depth of the slot 4 with respect to the bone. The dial 6 can include a plurality of rotatable positions corresponding to a plurality of cutting depths of the slot 4. For example, a first position of the dial 6 can correspond to a minimum cutting depth of the slot 4, and a second position of the dial 6 can correspond to a maximum cutting depth of the slot 4. As the dial 6 is rotated, in the first direction, past the second position, the slot 4 can return directly to the minimum cutting depth. Returning directly to the minimum cutting depth can provide a surgeon with fast return depth adjustment capabilities, which can reduce the amount of time spent adjusting the depth of the cutting block 2, relative to the bone, during an orthopedic procedure. The resection tower 12 can further include one or more longitudinal posts 11 configured to couple the resection tower 12 with the valgus guide 14.

The valgus guide 14 can adjust the varus/valgus angle of the cutting block 2. The valgus guide 14 can include a valgus alignment guide 16, a rotatable member 18, and a collet lock 20. The valgus alignment guide 16 can have one or more lumens to receive the one or more longitudinal posts 11 of the resection tower 12, thereby allowing the resection tower 12 to couple to the valgus guide 14. The rotatable member 18 can include an angular surface with one or more variable depth splines, such as those illustrated as reference numerals 182, 184 in FIGS. 11 and 12, below. The splines can enable a maximum varus/valgus angle to be reached by rotating the rotatable member 18 less than 90 degrees. In an example, the maximum varus/valgus angle can be reached by rotating the rotatable member 18 between 50 and 60 degrees, such as about 56 degrees. The collet lock 20 can couple the valgus guide 14 to a previously positioned intramedullary rod or nail (not shown) to secure the valgus guide 14 to a bone and provide for accurate placement of the cutting block 2. The collet lock 20 can increase operating room efficiency by enabling the valgus guide 14 to be secured to the intramedullary rod or nail, instead of pinning the valgus guide 14, to a distal end of a femur, for example.

Figure 2:
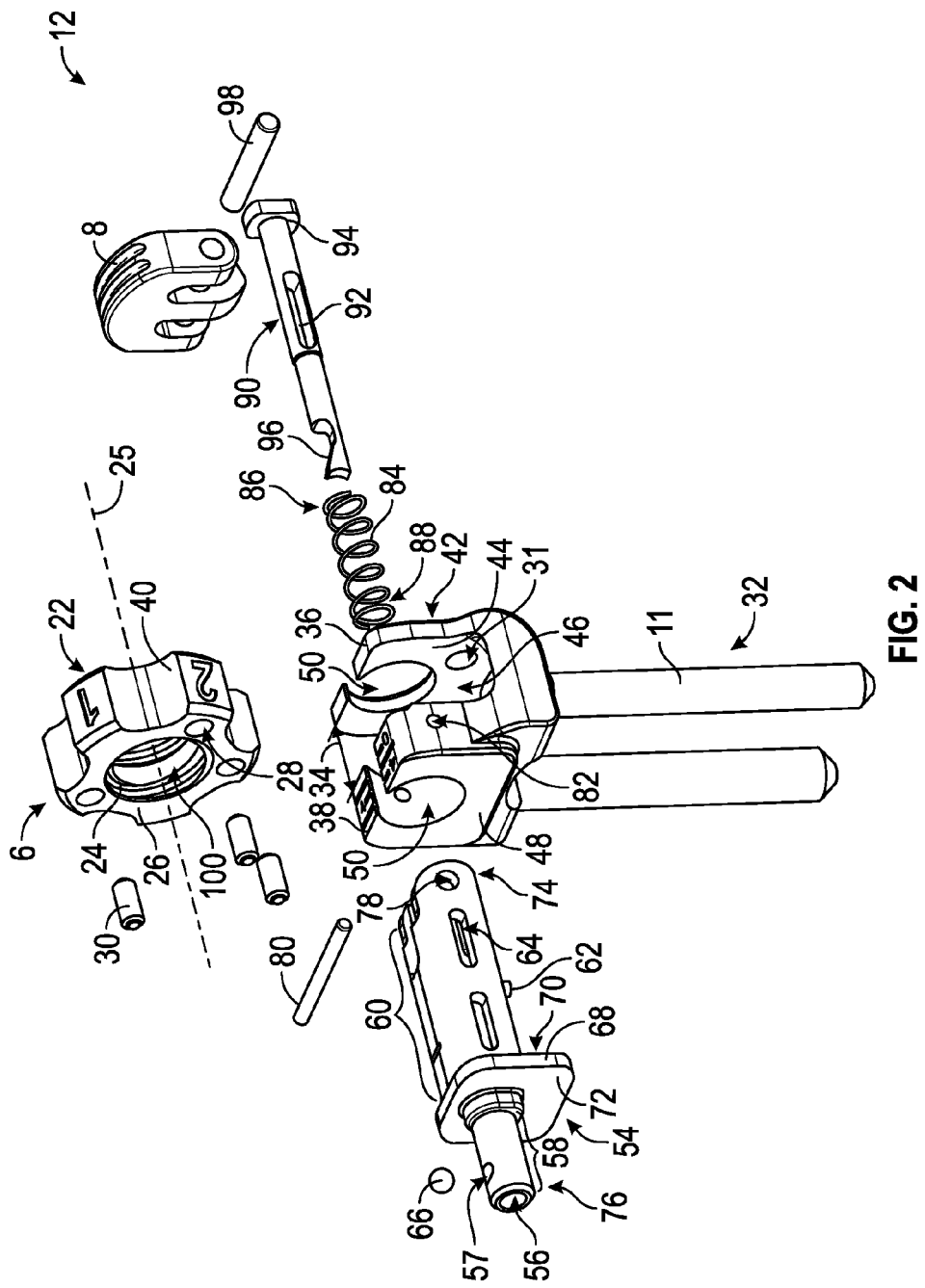
FIG. 2 illustrates an exploded view of a portion of the resection tower of FIG. 1, in accordance with at least one example of the present disclosure.

FIG. 2 illustrates an exploded view of a portion of the resection tower 12 of FIG. 1, in accordance with at least one example of the present disclosure. The portion of the resection tower 12 illustrated in FIG. 2 excludes the cutting block 2 (which is illustrated in FIG. 1). As illustrated in FIG. 2, the resection tower 12 can include the dial 6, a pin 54, a base 32, a plunger 90, and a resilient member 84. The dial 6 can include a first side 22, a second side 26, and an internal surface 24 defining a bore 100 extending along an axis 25 between the first side 22 and the second side 26. The internal surface 24 can include a helical groove extending from a first point, adjacent to the first side 22, to a second point, adjacent to the second side 26. Additionally, the dial 6 can include a substantially straight groove extending from the first point to the second point.

The pin 54 can be longitudinally disposed in a direction substantially parallel to the axis 25. The pin 54 can include a first end portion 60 and a second end portion 58, the latter of which is releasable coupled with the cutting block 2. The pin 54 can include a projection 62 extending from the first end portion 60 at an angle relative to the longitudinal disposition of the pin 54. The projection 62 can be configured to move along the helical groove as the dial 6 is rotated from a first position associated with the first point, which corresponds to the minimum cutting depth of the slot 4, to a second position associated with the second point, which corresponds to the maximum cutting depth of the slot 4. The projection 62 can also be configured to move along the substantially straight groove as the dial 6 is rotated, in the first direction, past the second positioned to return the slot 4 directly to the minimum cutting depth.

The base 32 can include one or more longitudinal posts 11, a first holding block 36, and a second holding block 38. The one or more longitudinal posts 11 can couple the resection tower 12 to the valgus guide 14. The first holding block 36 and the second holding block 38 can be separated by a space 34. The space 34 can be configured to receive a portion of the dial 6 such that the dial 6 can rotate about the axis 25 within the space 34. The first holding block 36 and the second holding block 38 can each include an opening 50 extending from a first surface 42, 46 of the first and second holding blocks 36, 38, to a second surface 44, 48 of the first and second holding blocks 36, 38. When assembled, the first portion 60 of the pin 54 can extend through the opening 50 in the second holding block 38, the bore 100 of the dial 6, and the opening 50 in the first holding block 36. The second portion 60 of the pin 54 can be movable along the axis 25 with respect to the dial 6 and the base 32 to adjust the cutting depth of the slot 4.

The dial 6 can be coupled to the base 32 via locking pegs 30. The dial 6 can include a plurality of positions corresponding to a plurality of cutting depths of the slot 4. The locking pegs 30 are configured such that each position of the plurality of positions aligns at least one of the locking pegs 30 with one of the openings 31 in the first holding block 36 to maintain the dial 6 at a particular position. For example, when the at least one locking peg 30 is aligned with one of the openings 31, the at least one locking peg 30 can partially extend into the opening 31.

The plunger 90 can be part of a locking mechanism configured to releasable couple the second end portion 58 of the pin 54 to the cutting block 2. The locking mechanism can also include a locking lever 8 and a locking ball 66. The plunger 90 can include a ramped surface 96 and can extend within a bore 54 of the pin 54. The ramped surface 96 can be positioned, when assembled, near the second end portion 58 of the pin 54 such that the ramped surface 96 can engage with the locking ball 66. The locking ball 66 can secure the engagement between the pin 54 and the cutting block 2 when the locking lever 8 is in a locked position. The ramped surface 96 can interact with the locking ball 66 as the locking lever 8 is transitioned from an unlocked position to the locked positioned to couple the cutting block 2 to the pin 54. For example, when the locking lever 8 is in the locked position, the ramped surface 96 and the locking ball 66 interact such that the locking ball 66 partially extends through a locking hole 57 positioned toward a second end 76 of the pin 54. While in the locked position, the locking ball 66 can partially extend into a corresponding hole in the cutting block 2 to couple the cutting block 2 to the pin 54.

The pin 54 can be coupled to the locking lever 8 via openings 78 positioned towards a first end 74 of the pin 54. The openings 78 can receive a locking rod 98 that extends through the locking lever 8. As the locking lever 8 moves between the locked positioned and the unlocked position, the relationship between the ramped surface 96 and the locking ball 66 changes such that the locking 66 ball is substantially positioned within a bore 56 of the pin 54 and uncouples the cutting block 2 from the pin 54.

The pin 54 and the plunger 90 can be coupled to the base 32. For example, the pin 54 can include first and second slots 64 extending along the first portion 60 of the pin 54. The first and second slots 64 are positioned directly across from each other and extend in a direction parallel to the axis 25. Additionally, the plunger 90 can include a slot 92 that extends in a direction parallel to the axis 25. A base rod 80 can extend through the first and second slots 64 of the pin 54, the slot 92 of the plunger 90, and wall openings 82 in the second holding block 38 to moveably couple the pin 54 and the plunger 90 to the base 32. When the pin 54 and the plunger 90 are coupled to the cutting block 2, the pin 54, the plunger 90, and the cutting block 2 can move along axis 25 as an integral unit, with respect to the base 32, to adjust the cutting depth of the slot 4.

Figure 6:
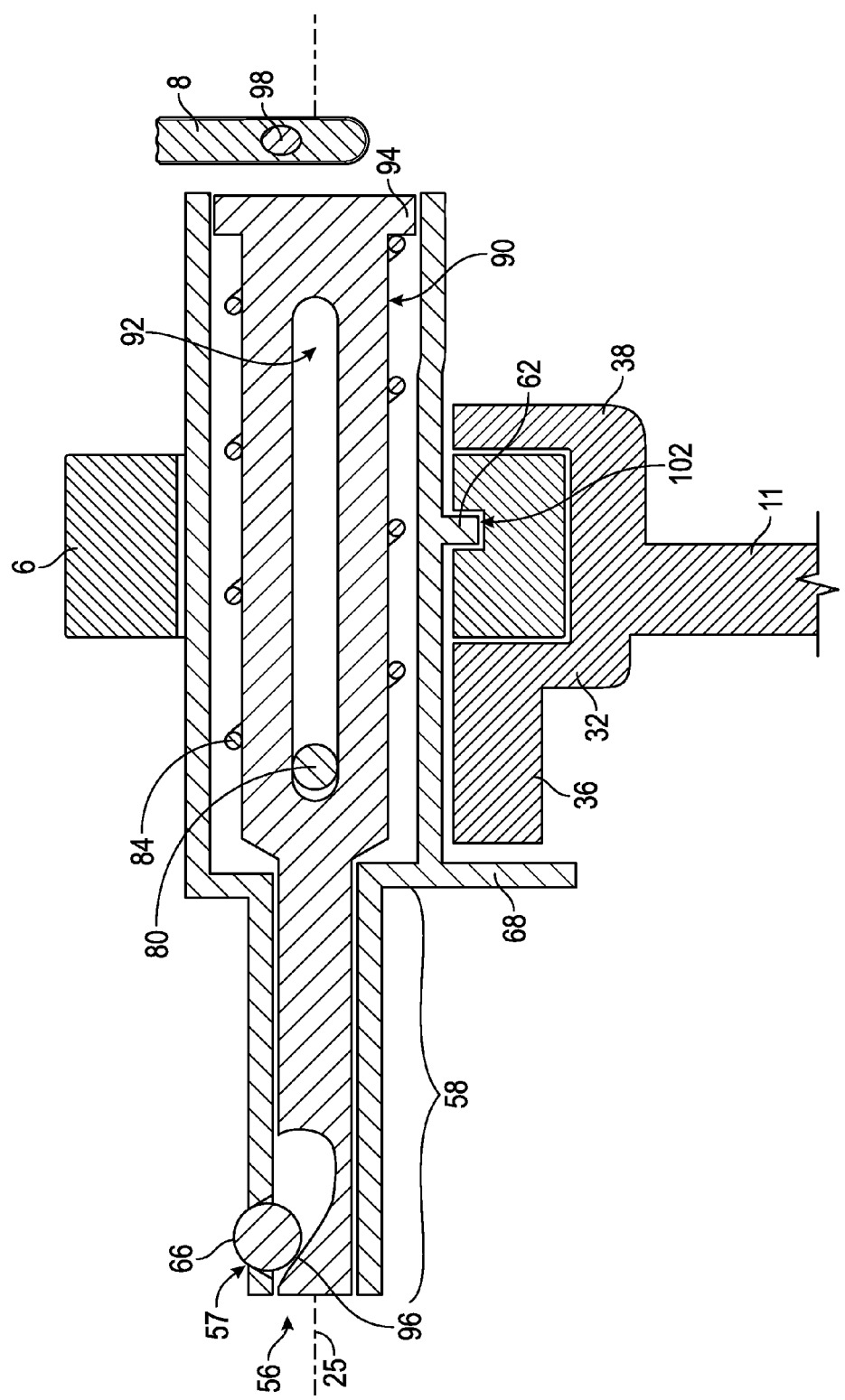
FIG. 6 illustrates a cross-sectional view of the portion of the resection tower of FIG. 5, such as along line 6-6.

The resilient member 84 includes a first end 86 and a second end 88. When assembled, the resilient member 84 can be positioned around the plunger 90 and within the first portion 60 of the pin 54 (as illustrated in FIG. 6). The first end 86 of the resilient member 84 can be positioned between a foot portion 94 of the plunger and the base rod 80. The resilient member 84 can be configured to be in an uncompressed state when the dial 6 is at the first position, corresponding to the minimum cutting depth of the slot 4, and can be configured to be in a compressed state when the dial 6 is at the second position, corresponding to the maximum cutting depth of the slot 4. For example, as the dial 6 is rotated, in the first direction, from the first position to the second position, the projection 62 can move within the helical groove of the dial 6 and compress the resilient member 84 between the foot portion 94 and the base rod 80. As the dial 6 is further rotated, in the first direction, past the second position, the projection 62 can become aligned with the substantially straight groove of the dial and the resilient member 84 can transition from the compressed state to the uncompressed state. As the resilient member 84 transitions from the compressed state to the uncompressed state, the projection 62 can move along the substantially straight groove and return the slot 4 directly to the first position, which corresponds to the minimum cutting depth of the slot 4.

Figure 3:
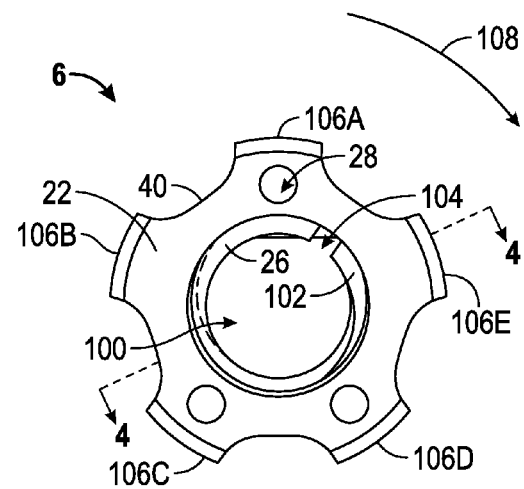
FIG. 3 illustrates a front view of a dial of a resection tower, in accordance with at least one example of the present disclosure.

FIG. 3 illustrates a front view of a dial 6, in accordance with at least one example of the present disclosure. An external surface 40 of the dial 6 can define a plurality of knobs 106A-106E (hereinafter generically referred to "knob 106" or collectively as "knobs 106"). Each knob 106 can represent a position of the dial 6, which in turn can represent a cutting depth of the slot 4. In the example of FIG. 3, the dial 6 includes five knobs 106; however, the dial 6 may include more or less than five knobs 106. The knob 106A can represent a minimum cutting depth that, when positioned at an upper-most dial location, corresponds to the minimum cutting depth of the slot 4. The knob 106E can represent a maximum cutting depth that, when positioned at the upper-most dial location, corresponds to the maximum cutting depth of the slot 4. The cutting depth of the slot 4 corresponding to each knob 106, when positioned at the upper-most dial location, can increase from knob 106A to knob 106E.

As further illustrated in FIG. 3, the internal surface 26 of the dial 6 can include the helical groove 102 and the substantially straight groove 104. As the dial 6 is rotated in the first direction 108 from the first position, associated with the knob 106A positioned at the upper-most dial location, to the second position, associated with the knob 106E positioned at the upper-most dial location, the cutting block 2 moves from the minimum cutting depth to the maximum cutting depth. The substantially straight groove 104 is positioned between helical groove positions associated with the knobs 106A and 106E, such that when the dial 6 is rotated past the second position, in the first direction 108, the cutting block 2 can return directly to the minimum cutting depth.

Figure 4:
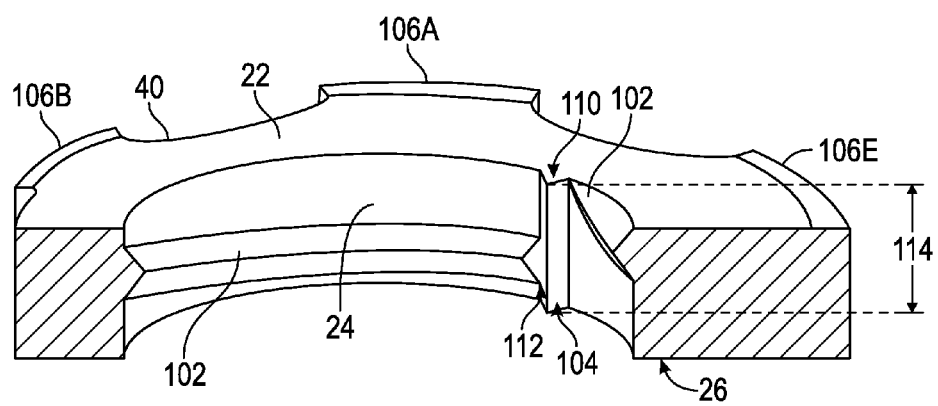
FIG. 4 illustrates a partial cross-sectional view of the dial of FIG. 3, such as along line 4-4.

FIG. 4 illustrates a partial cross-sectional view of the dial 6 of FIG. 3, such as along line 4-4. The internal surface 26 of the dial includes the helical groove 102. The helical groove can be in the form of a depression (e.g., an internal thread), as shown in FIG. 6, or the helical groove can be in the form of a projection (e.g., an external thread), as shown in FIG. 4. In either form, the helical groove 102 can be configured to engage the projection 62 of the pin 54.

In the example of FIG. 4, the helical groove 102 is an external thread that can interact with the projection 62 of the pin 54. The helical groove 102 can extend from a first point 110, adjacent to the first side 22 of the dial 6, to a second point 112, adjacent to the second side 26 of the dial 6. An axial distance 114 between the first point 110 and the second point 112 can substantially correspond to a distance between the minimum cutting depth and the maximum cutting depth of the slot 4. The helical groove 102 can extend less than 360 degrees around the internal surface 26. The substantially straight groove 104 can extend from the first point 110 to the second point 112 and is positioned between the first and second positions of the dial 6. That is, the substantially straight groove 104 is positioned between knob 106A, representing the minimum cutting depth of the slot 4, and knob 106E, representing the maximum cutting depth of the slot 4.

As the dial 6 is rotated in the first direction 108, from the first position to the second position, the projection 62 can move along the helical groove 102 from the first position 110 to the second position 112. As the projection 62 moves along the helical groove 102, the cutting depth of the slot 4 can be adjusted from the minimum cutting depth to the maximum cutting depth. As the dial 6 is rotated in the first direction 106, past the second position, the projection 62 can move along the substantially straight groove 104 from the second position 112 to the first position 110. As the projection 62 moves along the substantially straight groove 104, the cutting depth of the slot 4 can be adjusted from the maximum cutting depth directly to the minimum cutting depth. The resilient member 84, while the dial 6 is at the second position, can be configured to be in a compressed state such that when the projection 62 aligns with the substantially straight groove 104, the resilient member 84 transitions from the compressed state to the uncompressed state returning the slot 4 directly to the minimum cutting depth associated with the first position of the dial 6.

Figure 5:
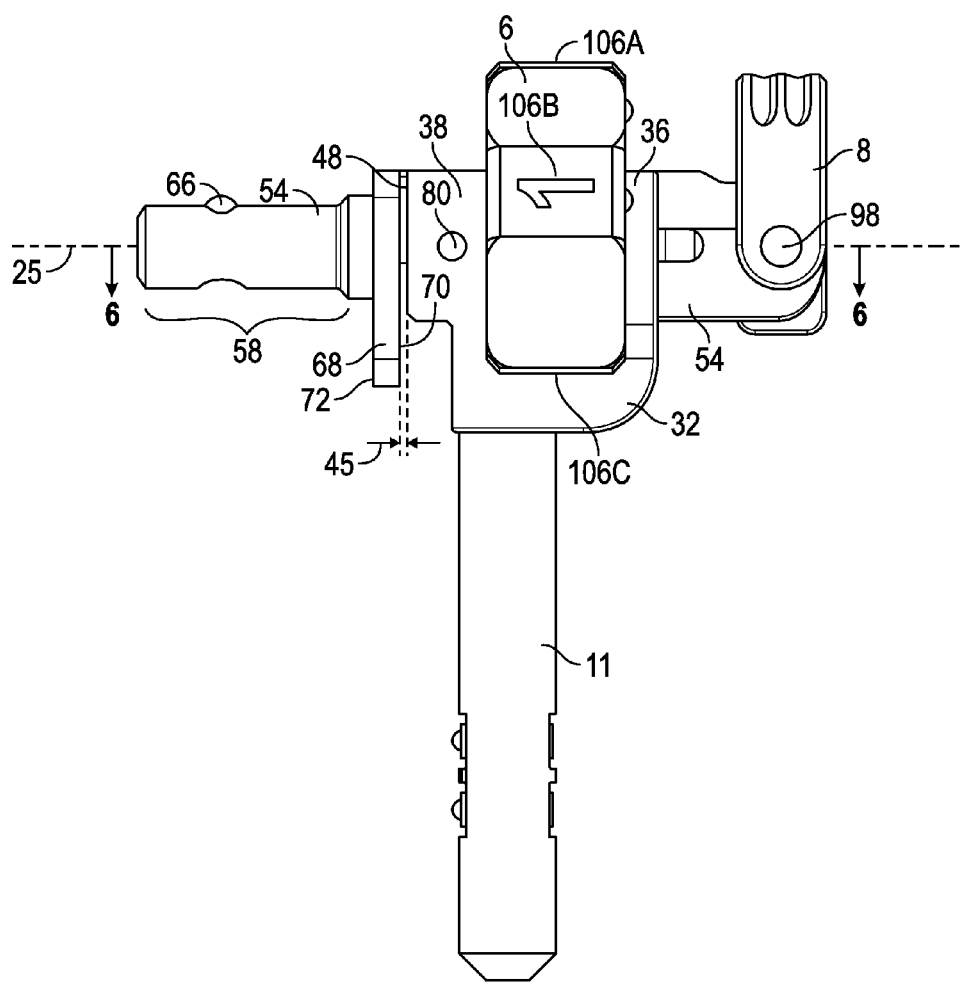
FIG. 5 illustrates a side view of a portion of the resection tower of FIG. 2, in accordance with at least one example of the present disclosure.

FIG. 5 illustrates a side view of the portion of the resection tower 12 of FIG. 2, in accordance with at least one example of the present disclosure. In FIG. 5, the dial 6 is shown in the first position (e.g., the knob 106A is positioned at an upper-most dial location), corresponding to the minimum cutting depth of the slot 2. The pin 54 can include a plate portion 68 that is positioned between the first portion 60 and the second portion 58 of the pin 54. The plate portion 68 can include a first surface 70 and a second surface 72. The first surface 70 is configured to face the second surface 44 of the second holding block 38. As the dial 6 is rotated in the first direction, from the first position to the second position, a distance 45 between the first surface 70 of the plate 68 and the second surface 48 of the second holding block 28 can increase. As the dial 6 is rotated in the first direction, past the second position to the first position, the distance 45 between the first surface 70 of the plate 68 and the second surface 48 of the second holding block 38 can decrease.

FIG. 6 illustrates a cross-sectional view of the portion of the resection tower 12 of FIG. 5, such as along line 6-6. The locking lever 8 is shown in a locked position and the locking ball 66 extends through the locking hole 57 of the pin 54. The ramped surface 96 can interact with the locking ball 66 and when the locking lever 8 is in the locked position, the locking ball 66 can move along the ramped surface 96 and extend through the locking hole 57. When the locking lever 8 is transitioned to an unlocked positioned, such as by rotating the locking lever 8 about locking rod 98, the plunger 90 can move with respect to the pin 54 and the locking ball 66 can move along the ramped surface 97 and be positioned substantially within the bore 56 of the pin 54. In the unlocked position, the locking ball 66 does not engage the corresponding hole in the cutting block 2 and the pin 54 and the cutting block 2 can be separated.

In the example of FIG. 6, the projection 62 is positioned within a helical groove 102, in the form of an internal thread, and the resilient member 84 is positioned between the base rod 80 and the foot portion 93 of the plunger 90. As shown, the projection 62 extends from a bottom surface of the pin 54. However, the projection 62 can also extend from the top surface of the pin 54.

As the dial 6 is rotated in the first direction from the first position to the second position, the projection 62 can move along the helical groove 120 causing the pin 54 and plunger 90 to move linearly with respect to the base 32 and the dial 6. When the pin 54 and the plunger 90 are coupled to the cutting block 2, the pin 54, the plunger 90, and the cutting block 2 can move along axis 25 as an integral unit with respect to the base 32 to adjust the cutting depth of the slot 4.

The resilient member 84 can be configured to be in an uncompressed state when the dial 6 is at the first position, corresponding to the minimum cutting depth of the slot 4, as illustrated in FIG. 6. As the dial 6 is rotated in the first direction from the first position to the second positioned, the projection 62 can move within the helical groove 102 can cause the resilient member to transition to a compressed state. For example, the resilient member 84 is positioned between the base rod 80 and the foot portion 94 of the plunger 90. As the pin 54 and plunger 90 move along axis 25 with respect to base rod 80, the resilient member becomes compressed as a distance between the base rod 80 and the foot portion 94 decreases.

When the dial 6 is rotated in the first direction past the second position, the projection 62 can become aligned with the substantially straight groove (shown as reference number 104 in FIGS. 3 and 4) and the resilient member 84 can transition from the compressed state to the uncompressed state. As the resilient member 84 transitions from the compressed state to the uncompressed state, the projection 62 moves along the substantially straight groove and the slot 4 can return directly to the minimum cutting depth, which corresponds to the first position of the dial 6.

Figure 7:
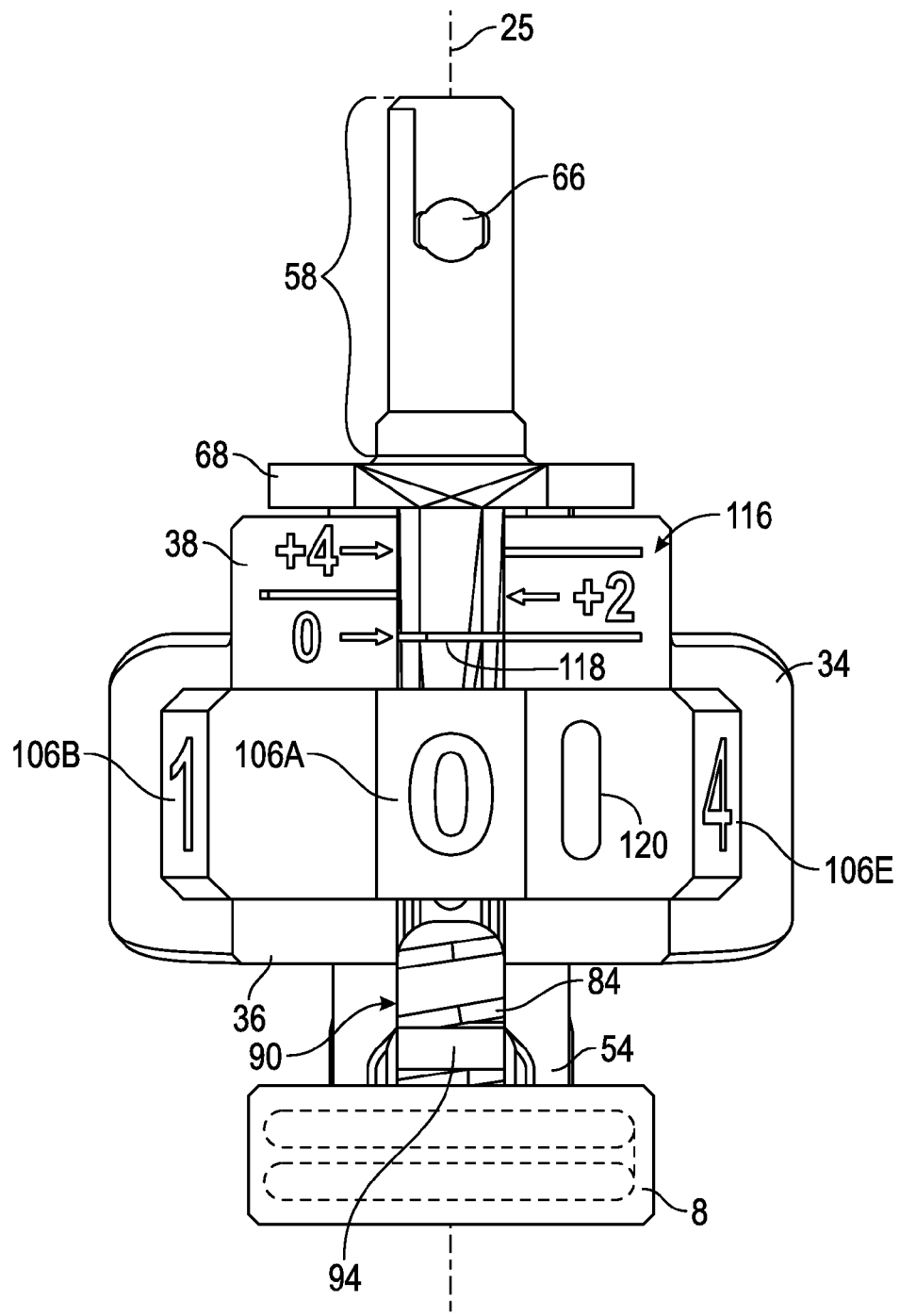
FIG. 7 illustrates a top view of the portion of the resection tower of FIG. 5, in accordance with at least one example of the present disclosure.

FIG. 7 illustrates a top view of the portion of the resection tower 12 of FIG. 5, in accordance with at least one example of the present disclosure. As shown, the dial 6 is in the first position corresponding to the minimum cutting depth of the slot 2. The knobs 106 can include markings to indicate a cutting depth associated with each knob 106, when positioned at an upper-most dial location. By way of example, knob 106A can include a "0" marking indicating that the cutting block 2 is at the minimum cutting depth (e.g., zero millimeters) and knob 106E can include a "4" marking indicating that the cutting block 2 is at the maximum cutting depth (e.g., 4 millimeters). The substantially straight groove can be positioned between knob 106A and 106E enabling the slot 4 to return to the minimum cutting depth when the dial 6 is rotated in the first direction past the second position. In this example, the second position is associated with knob 106E positioned at the upper-most dial location. In an example, the dial 6 can include an opening 120 that is in communication with the substantially straight groove.

The pin 54 can also include a depth gauge 118 that aligns with reference markings 116 on the second holding block 38 to indicate a cutting depth of the slot 4. When the dial 6 is at the first position, corresponding to the minimum cutting depth of the slot 4, the depth gauge 118 can be aligned with the "0" reference marking 116 indicating that the cutting depth of the slot 4 is at the minimum cut depth. When the dial 6 is at the second position, corresponding to the maximum cutting depth of the slot 4, (e.g., four millimeters), the depth gauge 118 can be aligned with the "+4" reference marking 116.

Figure 8:
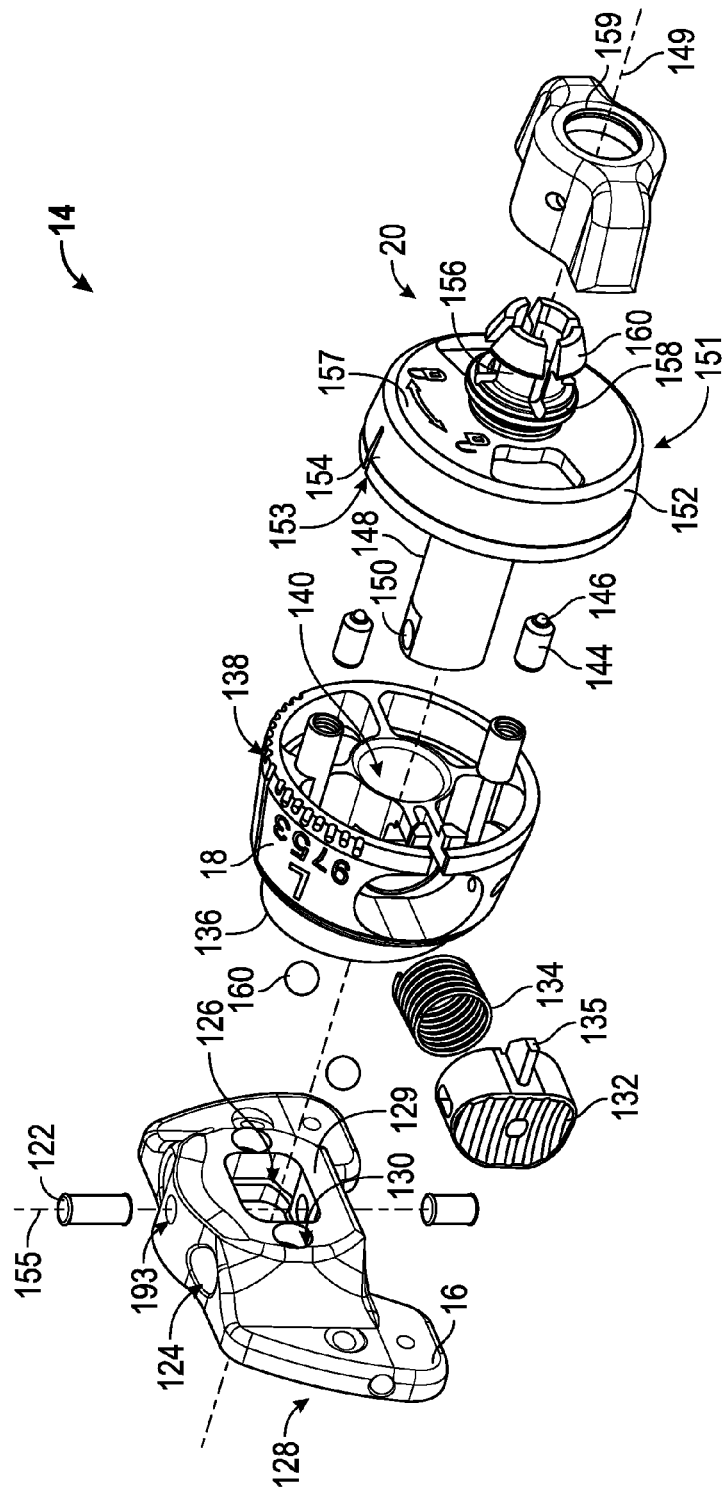
FIG. 8 illustrates an exploded view of the valgus guide of FIG. 1, in accordance with at least one example of the present disclosure.

FIG. 8 illustrates an exploded view of the valgus guide 14 of FIG. 1, in accordance with at least one example of the present disclosure. The valgus guide 14 can include a valgus alignment guide 16 and a rotatable member 18. The valgus alignment guide 16 can include one or more slots 124 configured to receive the one or more longitudinal posts 11 of the resection tower 12 (as illustrated in FIG. 1) to couple the valgus guide 16 to the resection tower 12. The valgus alignment guide 16 can include a first surface 128 and a second surface 129, which is opposite the first surface 128. The first surface 128 can be a bone contacting surface and the second surface 129 can include one or more depressions 130. The valgus alignment guide 16 can further include one or more spherical contacts 160 positioned partially within the one or more depressions 130. The valgus guide 16 can further include an alignment port 126 that is configured to receive at least an intramedullary rod or nail and rotate about a rotation axis 193 to adjust the varus/valgus angle of the cutting block 2.

Figure 11:
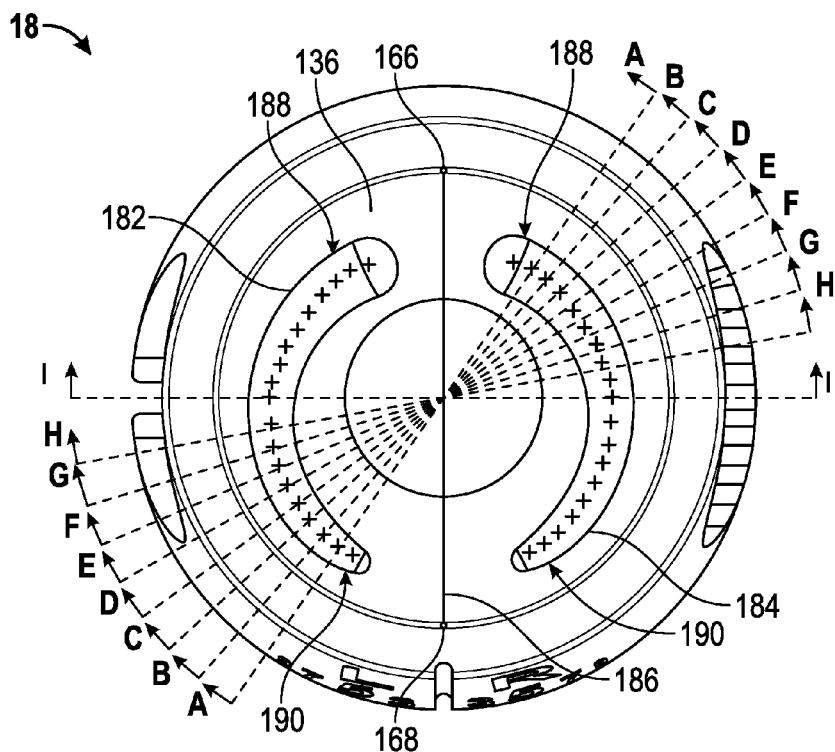
FIG. 11 illustrates an angular surface view of a rotatable member of a valgus guide, in accordance with at least one example of the present disclosure.
Figure 12A:
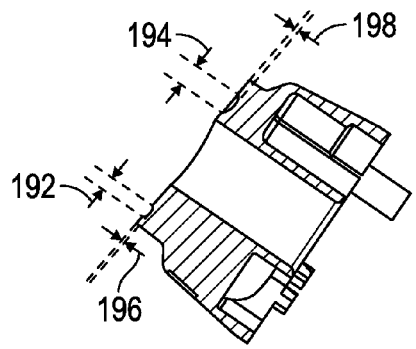
FIGS. 12A-I illustrate cross-sectional views of the rotatable member of FIG. 11, along lines A-A to I-I.
Figure 12D:
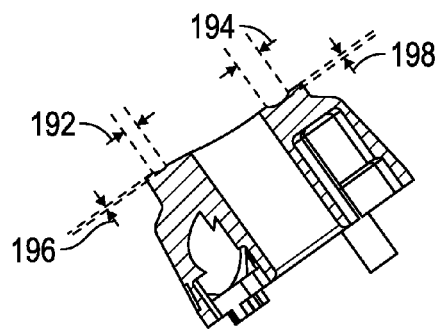
Figure 12B:
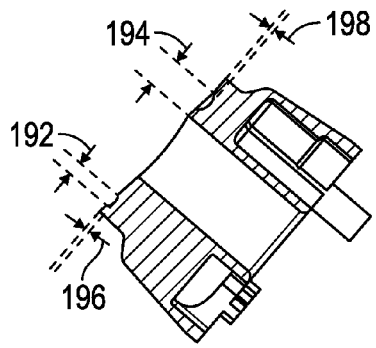
Figure 12E:
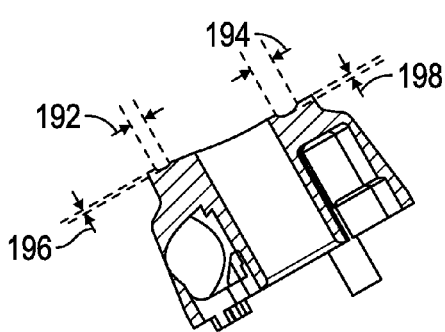
Figure 12C:
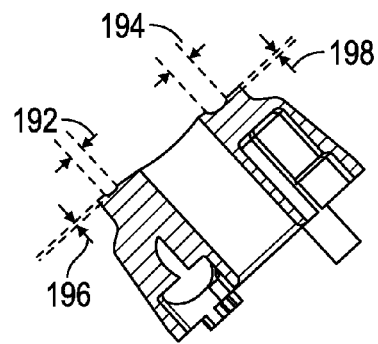
Figure 12F:
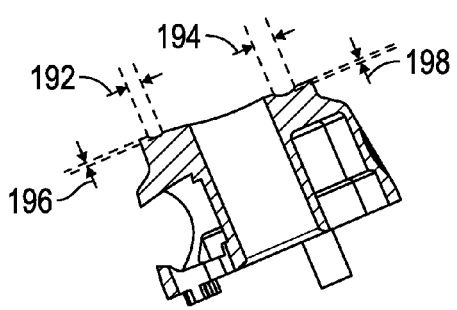
Figure 12G:
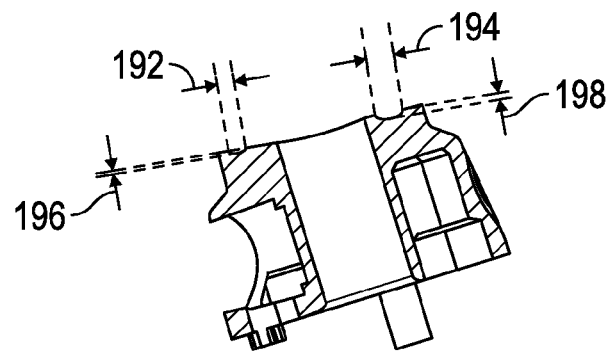
Figure 12H:
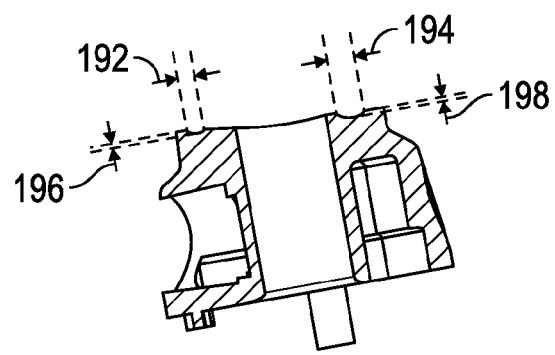
Figure 12I:
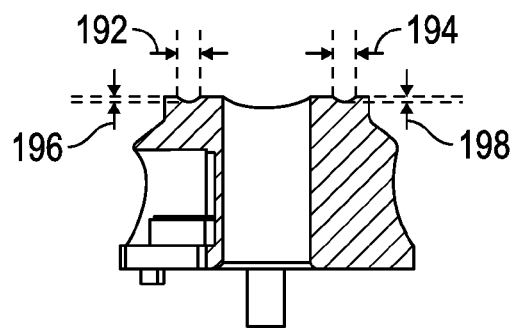

The rotatable member 18 can include an angular surface 136 with one or more variable depth splines (illustrated in FIG. 11 as reference numbers 182 and 184). The rotatable member 18 can include a bore 140 that is configured to receive the intramedullary rod or nail. The intramedullary rod or nail can be configured to extend through the bore 140 and the alignment port 124. The one or more spherical contacts 160 can engage with the one or more variable depth splines such that, when rotated, the rotatable member 18 can effectuate adjustment of a varus/valgus angle of the cutting block 2 by rotating the valgus alignment guide 16 about the rotation axis 192.

The valgus guide 14 can further include a reference member 151 having a reference base 152, a rotation post 148, and a locking post 156. The rotation post 148 can extend from a first side 153 of the reference base 152 and the locking post 156 can extend from a second side 157 of the reference base 152. The reference member 151 can be coupled to the valgus alignment guide 16 and the rotatable member 18. For example, the rotation post 148 can extend through the bore 140 of the rotatable member 18 and into the adjustment port 126 of the valgus alignment guide 16. The valgus alignment guide 16 can include rotation holes 193 that can be aligned with openings 150 that extend through the rotation post 148. When assembled, the rotation holes 193 and the openings 150 can be configured to receive rotation pins 122 such that the valgus alignment guide 16 can rotate about the rotation axis 155. The rotation axis 155 can extend centrally through the rotation holes 193 and the openings 150 and be substantially perpendicular with respect to a longitudinal axis 149 of the valgus guide 14. The valgus guide 14 can also include a locking hole and a locking pin configured to secure the valgus guide to a distal end of a bone.

The rotatable member 18 can be coupled to the reference member 151. For example, the rotatable member 18 can be coupled to the reference member 151 via a primary locking mechanism and a secondary locking mechanism. The primary locking mechanism can include a lock 132 and a resilient member 134. The primary locking mechanism, when locked, can prevent rotation of the rotatable member 18. The lock 132 can include a projection 135 that is configured to extend into and engage a first indentation positioned on the first side 153 of the reference body 152. In response to an applied force, the lock 132 can compress the resilient member 134 and the projection 135 can disengage from the indentation. Once disengaged, the rotatable member 18 can rotate about the longitudinal axis 149.

The secondary locking mechanism can assist in guiding the rotatable member 18 to a particular varus/valgus angle. The first side 153 of the reference base 152 can include a plurality of second indentations configured to be engaged with pins 144 of the rotatable member 18. The pins 144 can couple to the rotatable member and include the compressible members 146. When the rotatable member 18 is rotated while the primary locking mechanism is in an unlocked state, the compressible members 146 can compress into the pins 144 and enable the rotatable member 18 to rotate. For each varus/valgus angle, the pins 144 can align with one or more of the plurality of second indentations to assist in guiding the rotatable member 18 to a particular varus/valgus angle. That is, the pins 144 can engage one or more second indentations when the rotatable member 18 is rotated to each varus/valgus angle.

The rotatable member 18 can further include the collet lock 20. The collet lock 20 can include the locking post 158 and a turn knob 159. The locking post 156 can include a plurality of threads 158 configured to engage corresponding threads along an internal surface of the turn knob 159. The locking post 156 can include a plurality of flexible pegs 160. A bore 142 extending through the reference member 151 can be configured to receive the intramedullary rod or nail. As the turn knob 159 is turned in a first direction 161, the flexible pegs 160 can compress onto the intramedullary rod or nail and couple the valgus guide 14 to the intramedullary rod or nail. When the turn knob 159 is turned in a second direction 162, the flexible pegs 160 can release the intramedullary rod or nail and uncouple the valgus guide 14 from the intramedullary rod or nail.

Figure 9:
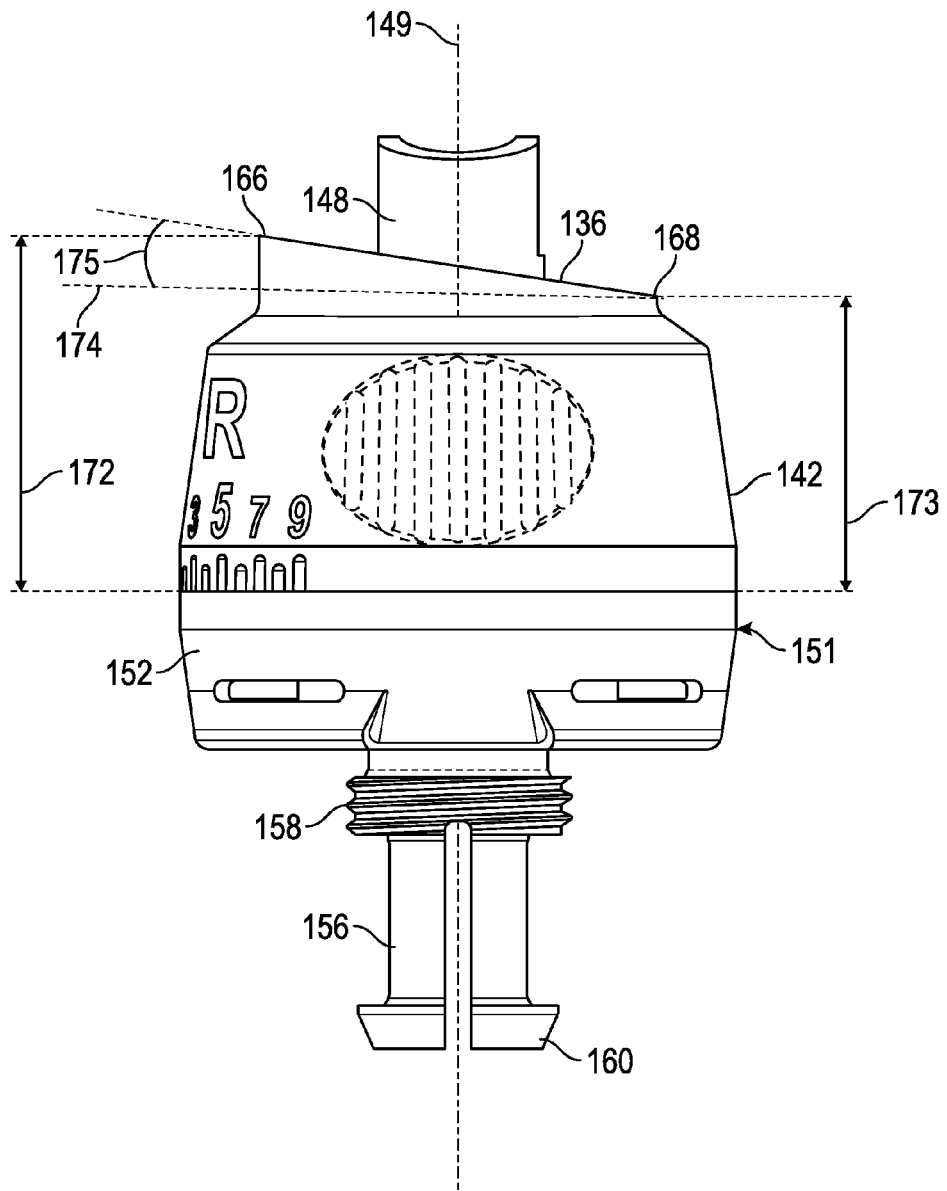
FIG. 9 illustrates a perspective view of a portion of the valgus guide of FIG. 8, in accordance with at least one example of the present disclosure.

FIG. 9 illustrates a perspective view of a portion of the valgus guide 14 of FIG. 8, in accordance with at least one example of the present disclosure. As shown in FIG. 9, the rotatable member 18 can be coupled to the reference member 151. A thickness 172 of the rotatable member 18 can be greatest at a first point 166 on the circumference of the angular surface 136. A thickness 173 of the rotatable member 18 can be smallest at a second point 168, diametrically opposite the first point 166, on the circumference of the angular surface 136. The angled surface 136 can form an angle 170 relative to a plane 174 perpendicular to the longitudinal axis 149 of the rotatable member. The angle 170 can correspond to a maximum left varus/valgus angle of the cutting block 2 and a maximum right varus/valgus angle of the cutting block 2.

Figure 10:
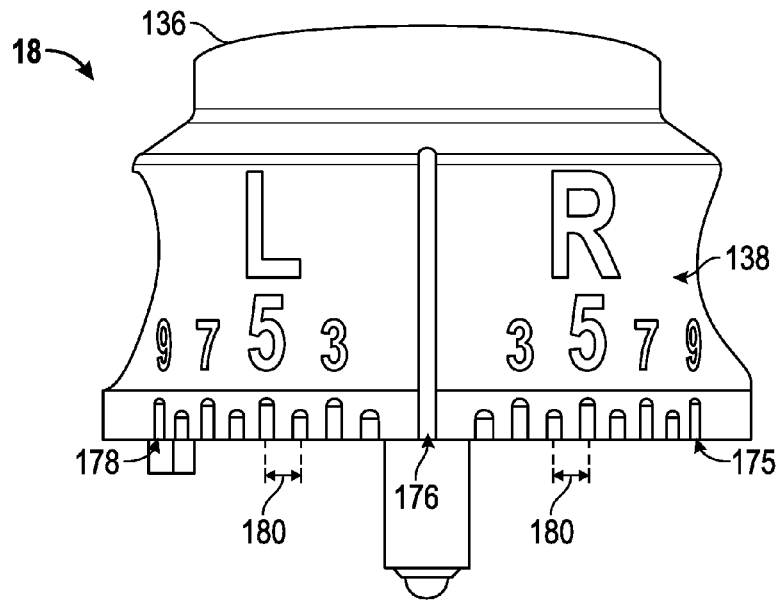
FIG. 10 illustrates a perspective view of a rotatable member of a valgus guide, in accordance with at least one example of the present disclosure.

FIG. 10 shows an example of a rotatable member 18. The rotatable member 18 can include a plurality of angle reference marks 138 corresponding to a plurality of varus/valgus angles. The plurality of angle reference marks 138 can include a center reference mark 176 corresponding to a minimum varus/valgus angle, a right maximum reference mark 175 corresponding to a maximum right varus/valgus angle, and a left maximum reference mark 178 corresponding to a maximum left varus/valgus angle. A space 180 between each of the plurality of angle reference marks 136 can be identical. In an example, each reference mark of the plurality of reference marks 136 can correspond to a same relative adjustment to the varus/valgus angle. As shown in the example of FIG. 10, the rotatable member can have a maximum right varus/valgus angle and a maximum left varus/valgus angle of nine degrees. In addition, by turning the rotatable member 18 one reference mark 138, a user can adjust the varus/valgus angle by, for example, one degree.

FIG. 11 illustrates a perspective view of a rotatable member, in accordance with at least one example of the present disclosure. The angled surface 136 of the rotatable member can include a first variable depth spline 182 and a second variable depth spline 184. The first and second variable depth splines 182, 184 can be positioned equidistant from a center line 186 connecting the first and second points 166, 168 on the circumference of the angular surface 136. The first and second variable depth splines 182, 184 can taper in width from a first end 188, near the first point 166 on the circumference, to a second end 190, near the second point 168 on the circumference, as shown in FIGS. 12A-12I. The first and second variable depth splines 182, 184 can form an arc between the first and second ends 188, 190. The first and second variable depth splines 182, 184 can have a first depth at the first end 188 and can have a second depth at the second end 190, where the first depth is greater than the second depth, as incrementally shown in FIGS. 12A-12I. The first and second variable depth splines 182, 184 enable the spacing 180 between the reference markings 136 (as illustrated in FIG. 10) to be identical. Additionally, the variable depth splines 182, 184 enable the maximum right varus/valgus angle and the maximum left varus/valgus angle to be reached by rotating the rotatable member 18 less than 90 degrees. In an example, the maximum right and left varus/valgus angle can be reached by rotating the rotatable member 18 plus or minus fifty-six degrees (+/−56°).

FIGS. 12A-12I illustrate cross-sectional views of the rotatable member of FIG. 11, such as along lines A-A to I-I. As illustrated in FIGS. 12A-12I, the depth and width of the first and second variable depth splines 182, 184 can vary from the first end 188 to the second end 190. The depth and width can vary based on the maximum right and left varus/valgus angle and an amount of rotation of the rotatable member 18 to reach the maximum right and left varus/valgus angle. In the example of FIGS. 12A-12I, the maximum right and left varus/valgus angle is plus or minus nine degrees (+/−9°) and the amount of rotation to reach the maximum right and left varus/valgus angle is approximately plus or minus fifty-six degrees (+/−56°). The width 192 of the first variable depth spline 182 and the width 194 of the second variable depth spline 184 vary from the first end 188 to the second end 190 of the first and second variable depth splines 182, 184. The depth 196 of the first variable depth spline 182 and the depth 198 of the second variable depth spline 184 vary from the first end 188 to the second end 190. The widths 192, 194 and the depths 196, 198 for the first and second variable depth splines 182, 184, along lines A-A to I-I of FIG. 11, are provided by way of example in Table 1.

TABLE 1

| Line | Width (millimeters) | | Depth (millimeters) | |
|---|---|---|---|---|
| | First Variable depth Spline | Second Variable Depth Spline | First Variable depth Spline | Second Variable Depth Spline |
| A-A | 0.25 | 0.83 | 2.16 | 3.72 |
| B-B | 0.31 | 0.75 | 2.40 | 3.57 |
| C-C | 0.35 | 0.69 | 2.56 | 3.40 |
| D-D | 0.38 | 0.64 | 2.66 | 3.34 |
| E-E | 0.40 | 0.60 | 2.71 | 3.26 |
| F-F | 0.41 | 0.58 | 2.74 | 3.20 |
| G-G | 0.41 | 0.57 | 2.74 | 3.17 |
| H-H | 0.42 | 0.57 | 2.76 | 3.17 |
| I-I | 0.51 | 0.51 | 3.02 | 3.02 |

Figure 13:
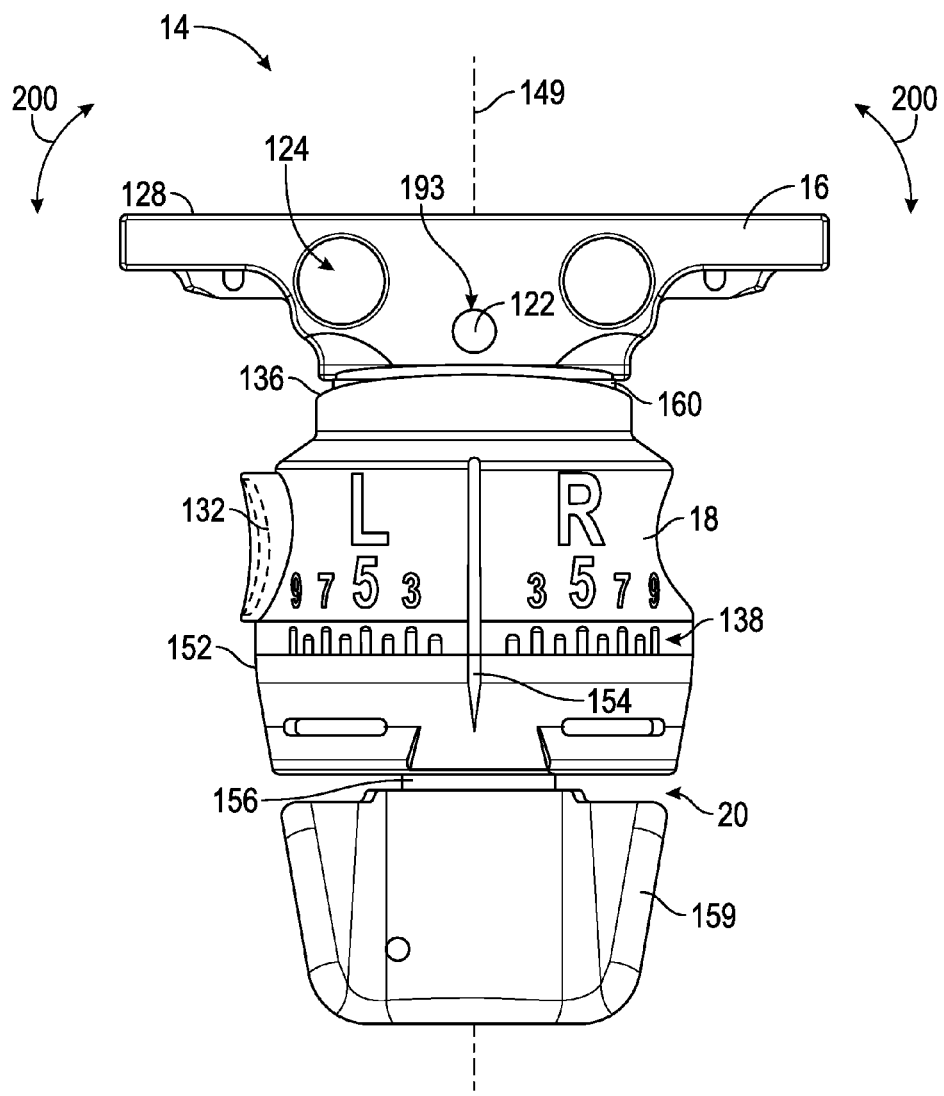
FIG. 13 illustrates a top view of a valgus guide, in accordance with at least one example of the present disclosure.

FIG. 13 illustrates a top view of a valgus guide 14, in accordance with at least one example of the present disclosure. The one or more spherical contacts 160 can engage with the one or more variable depth splines such that, when rotated, the rotatable member 18 can effectuate adjustment of a varus/valgus angle of the cutting block 2. For example, the valgus alignment guide 16 can rotate about the rotation axis (aligned with rotation pin 122) in a direction of the movement arrows 200 to adjust a varus/valgus angle of the cutting block 2. As shown in the example of FIG. 13, the reference base 152 can include an angle gauge 154 that can indicate the varus/valgus angle of the cutting block 2. The valgus guide 14 of the present disclosure can enable a maximum varus/valgus angle of the cutting block 2 to be reached by rotating the rotatable member 18 less than 90 degrees. Additionally, the collet lock 20 can secure the valgus guide 14 to an intramedullary rod or nail for accurate placement of the cutting block 2 instead of pinning the valgus alignment guide 16 to a distal end of a bone.

Figure 14A:
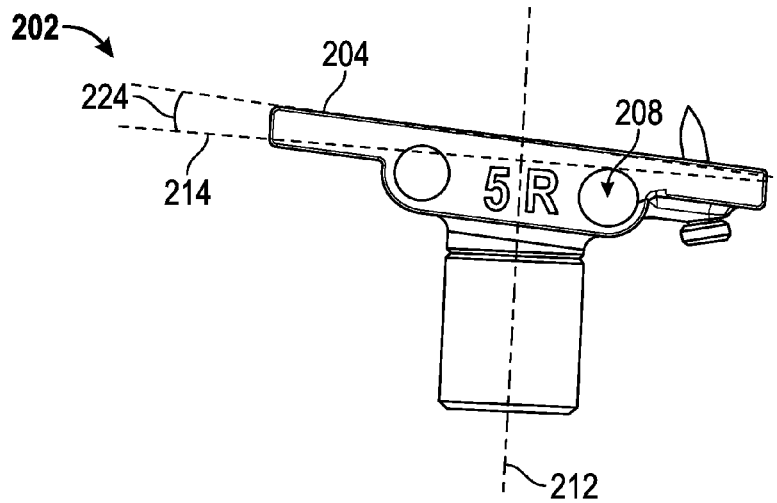
FIGS. 14A-C illustrate perspective views of a valgus guide, in accordance with at least one example of the present disclosure.
Figure 14B:
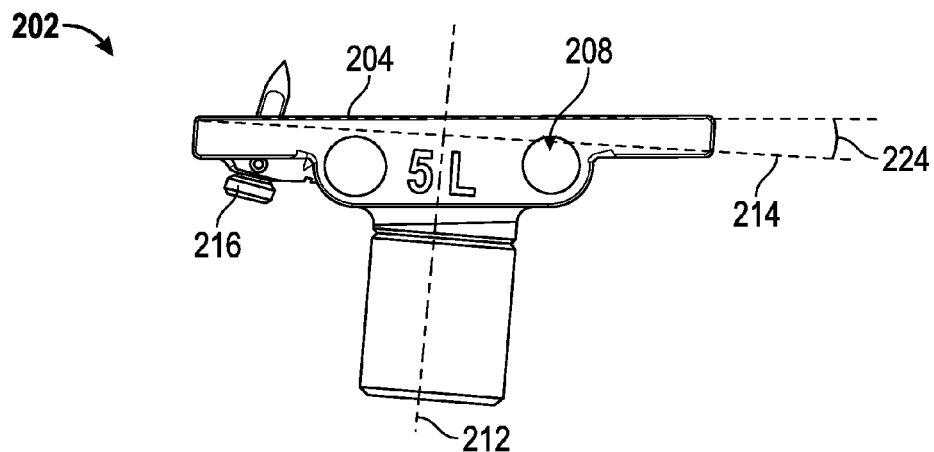
Figure 14C:
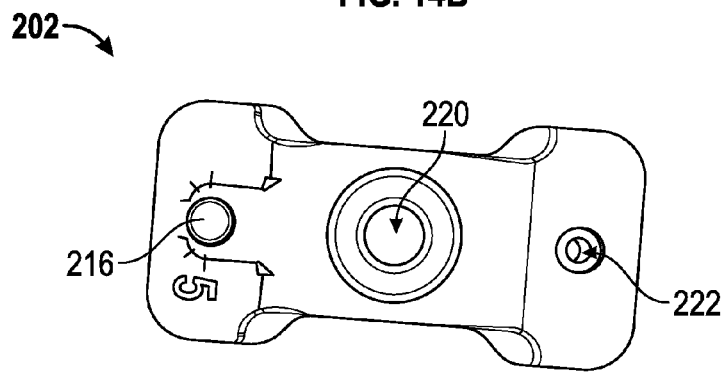

FIGS. 14A-C illustrate perspective views of a valgus guide 202, in accordance with at least one example of the present disclosure. The valgus guide 202 can be coupled with the resection tower 12. For example, the valgus guide 202 can include one or more slots 208 that can be configured to receive one or more longitudinal posts 11 of the resection tower 12. The valgus guide 202 can include a bore 220 (as illustrated in FIG. 14C) that can be configured to receive an intramedullary rod or nail. Depending on the orientation of the valgus guide 202 with respect to a bone, the valgus guide 202 can position the cutting block 2 at either a fixed right varus/valgus angle or a fixed left varus/valgus angle. As illustrated in FIGS. 14A and B, a bone contacting surface 204 can form an angle 224 with respect to a plane 214 that is perpendicular to a longitudinal axis 212 of the valgus guide 202. The angle 224 can correspond to the fixed right and left varus/valgus angle.

As illustrated in FIG. 14A, the valgus guide 202 can include a marking "5°R" indicating that the fixed varus/valgus angle is a five degree right varus/valgus angle. As illustrated in FIG. 14B, the valgus guide 202 can include a marking "5° L" indicating that the fixed varus/valgus angle is a five degree left varus/valgus angle. The valgus guide 202 can include a locking hole 222 and a locking pin 216 configured to secure the valgus guide 202 to a distal end of a bone.

Figure 15:
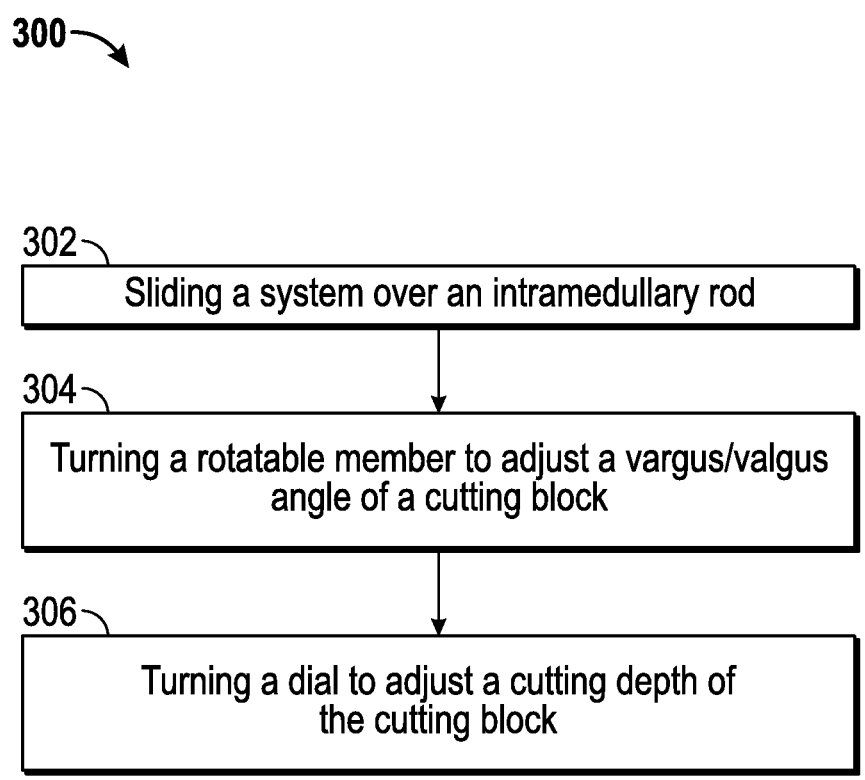
FIG. 15 illustrates a method of using a system including a resection tower and a valgus guide, in accordance with at least one example of the present disclosure.

FIG. 15 illustrates a method 300 of using a system including a resection tower and a valgus guide, in accordance with at least one example of the present disclosure. At 302, the method 300 can include sliding a system over an intramedullary rod or nail. The system can include a resection tower, having a cutting block and a dial, and a valgus guide, having a rotatable member, over an intramedullary rod or nail.

At 304, the method can include turning the rotatable member to adjust a varus/valgus angle of the cutting block. Turning the rotatable member can include engaging one or more spherical contacts with one or more variable depth splines on an angular surface of the rotatable member. In an example, turning the rotatable member less than 90 degrees can include positioning the cutting block at a maximum varus/valgus angle.

At 306, the method can include turning the dial to adjust a cutting depth of the cutting block. The dial can be turned in a first direction from a first position, corresponding to a minimum cutting depth of the cutting block, to a second position, corresponding to a maximum cutting depth of the cutting block. The dial, when turned in the first direction past the second position, can directly return the cutting block to the minimum cutting depth.

The above Detailed Description includes references to the accompanying drawings, which form a part of the Detailed Description. The drawings show, by way of illustration, specific embodiments in which the present surgical cutting guide systems and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In the event of inconsistent usages between this document and any document so incorporated by reference, the usage in this document controls.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the phrase "varus/valgus angle" is used to refer to a varus angle only, a valgus angle only, or both a varus angle and a valgus angle.

In the appended claims, the terms "including" and "in which" are used as the plain-English equivalents of the respective terms "comprising" and "wherein." The terms "including" and "comprising" are open-ended, that is, a system or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A system, comprising:
   a resection tower including a cutting block, having a slot for guiding a cutting tool, and a dial, coupled with the cutting block such that rotational movement of the dial about an axis effectuates movement of the cutting block along a plane substantially parallel with the axis,
   the dial, when rotated in a first direction, configured to move between a first position, corresponding to a minimum cutting depth of the slot, and a second position, corresponding to a maximum cutting depth of the slot, and
   the dial, when rotated in the first direction past the second position, causing the slot to return directly to the minimum cutting depth.

2. The system of claim 1, wherein the dial includes a first side, a second side, and an internal surface defining a bore extending about the axis between the first and second sides, the internal surface including a helical groove extending from a first point, adjacent to the first side, to a second point, adjacent to the second side.

3. The system of claim 2, wherein an axial distance between the first point and the second point along the internal surface substantially corresponds to a distance between the minimum cutting depth of the slot and the maximum cutting depth of the slot.

4. The system of claim 2, wherein the internal surface includes a substantially straight groove extending from the first point to the second point.

5. The system of claim 2, wherein the resection tower further includes a pin longitudinally disposed in a direction substantially parallel to the axis, the pin including a first end portion extending through the bore and a second end portion releasably coupled with the cutting block.

6. The system of claim 5, wherein the pin includes a projection, extending from the first end portion at an angle relative to the longitudinal disposition of the pin, configured to move along the helical groove from the first point to the second point as the dial is rotated in the first direction from the first position to the second position.

7. The system of claim 6, wherein the projection is configured to move along a substantially straight groove extending from the first point to the second point as the dial is rotated in the first direction from the second position.

8. The system of claim 5, wherein the resection tower further includes a base, to which the dial and the pin are coupled, and a locking mechanism configured to releasable couple the second end portion of the pin to the cutting block, the locking mechanism including:
   a locking lever, movable between a locked position and an unlocked position, coupled with the first end portion of the pin;
   a plunger, extending within the pin, including a locking ramped surface located near the second end portion of the pin; and
   a locking ball engageable with the locking ramped surface, the locking ball securing engagement between the pin and the cutting block when the locking lever is in the locked position.

9. The system of claim 8, further including a resilient member extending around the plunger from a first end to a second end, wherein the resilient member is configured to transition from a compressed state to an uncompressed state as the dial is rotated from the second position to the first position.

10. The system of claim 1, further comprising a valgus guide, coupled with the resection tower, including a rotatable member having an angular surface with one or more variable depth splines.

11. The system of claim 10, wherein the valgus guide further includes:
    a valgus alignment guide, through which the valgus guide is coupled with the resection tower, having one or more depressions; and
    one or more spherical contacts positioned partially within the one or more depressions and engaged with the one or more variable depth splines, wherein the rotatable member, when rotated, is configured to effectuate adjustment of a varus/valgus angle of the cutting block, and wherein a maximum varus/valgus angle is reached when the rotatable member is rotated less than 90 degrees.

12. The system of claim 11, wherein the rotatable member includes a plurality of angle reference marks corresponding to a plurality of varus/valgus angles, the plurality of angle reference marks include at least a center reference mark corresponding to a minimum varus/valgus angle, a right maximum reference mark corresponding to a maximum right varus/valgus angle, and a left maximum reference mark corresponding to a maximum left varus/valgus angle.

13. The system of claim 10, wherein a thickness of the rotatable member is greatest at a first point on the circumference of the angular surface and is smallest at a second point, diametrically opposite the first point, on the circumference of the angular surface.

14. The system of claim 13, wherein the angular surface comprises a first variable depth spline and a second variable depth spline, the first and second variable depth splines positioned equidistant from a center line connecting the first and second points on the circumference of the angular surface.

15. The system of claim 13, wherein the one or more variable depth splines taper in width from a first end, near the first point on the circumference, to a second end, near the second point on the circumference, and wherein the one or more variable depth splines form an arc between the first and second ends.

16. The system of claim 15, wherein the one or more variable depth splines have a first depth at the first end and have a second depth at the second end, the first depth greater than the second depth.

17. The system of claim 10, wherein the valgus guide includes a collet lock configured to couple to an intramedullary rod or nail.

18. A method, comprising:
sliding a system including a resection tower, having a cutting block and a dial, and a valgus guide, having a rotatable member, over an intramedullary rod or nail;
turning the rotatable member to adjust a varus/valgus angle of the cutting block, including engaging one or more spherical contacts with one or more variable depth splines on an angular surface of the rotatable member; and
turning the dial to adjust a cutting depth of the cutting block, wherein turning the dial includes turning the dial in a first direction from a first position, corresponding to a minimum cutting depth of the cutting block, to a second position, corresponding to a maximum cutting depth of the cutting block, and wherein turning the dial in the first direction further includes turning the dial past the second position, thereby directly returning the cutting block to the minimum cutting depth.

19. The method of claim 18, wherein turning the rotatable member includes turning the rotatable member less than 90 degrees and positioning the cutting block at a maximum varus/valgus angle.

\* \* \* \* \*

UNITED STATES PATENT AND TRADEMARK OFFICE
CERTIFICATE OF CORRECTION

| | | |
|---|---|---|
| PATENT NO. | : 9,204,897 B2 | Page 1 of 1 |
| APPLICATION NO. | : 13/720251 | |
| DATED | : December 8, 2015 | |
| INVENTOR(S) | : Jones et al. | |

It is certified that error appears in the above-identified patent and that said Letters Patent is hereby corrected as shown below:

In the Claims

In column 16, line 5, in Claim 8, delete "releasable" and insert --releasably--, therefor Signed and Sealed this
Twenty-sixth Day of April, 2016

Michelle K. Lee
*Director of the United States Patent and Trademark Office*